(12) United States Patent
Behan et al.

(10) Patent No.: US 7,547,523 B2
(45) Date of Patent: *Jun. 16, 2009

(54) HISTAMINE RECEPTOR

(75) Inventors: Jiang X. Behan, Edison, NJ (US);
Joseph A. Hedrick, South River, NJ (US); Thomas M. Laz, Parlin, NJ (US);
Frederick James Monsma, Jr., Summit, NJ (US); Kelley L. Morse, Livingston, NJ (US); Shelby P. Umland, Boonton Township, NJ (US); Suke Wang, Edison, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/620,337

(22) Filed: Jan. 5, 2007

(65) Prior Publication Data

US 2007/0117155 A1 May 24, 2007

Related U.S. Application Data

(60) Continuation of application No. 10/616,088, filed on Jul. 8, 2003, now Pat. No. 7,166,705, which is a continuation of application No. 09/812,216, filed on Mar. 19, 2001, now Pat. No. 6,613,533, which is a division of application No. 09/414,010, filed on Oct. 7, 1999, now Pat. No. 6,204,017.

(51) Int. Cl.
*G01N 33/567* (2006.01)
*C07K 14/705* (2006.01)

(52) U.S. Cl. .................. 435/7.21; 435/7.2; 436/501

(58) Field of Classification Search .................. None
See application file for complete search history.

(56) References Cited

U.S. PATENT DOCUMENTS

| 5,011,912 | A | 4/1991 | Hopp et al. |
| 5,817,480 | A | 10/1998 | Murry et al. |
| 6,204,017 | B1 | 3/2001 | Behan et al. |
| 6,613,533 | B2 | 9/2003 | Behan et al. |

FOREIGN PATENT DOCUMENTS

WO      WO 00/31258      6/2000

OTHER PUBLICATIONS

Voet et al., *Biochemistry*, John Wiley & Sons, Inc., pp. 126-128 and 228-234 (1990).
Birren et al., "*Homo sapiens* chromosome 18, clone RP11-178F10 unpublished", EMBL Sequence Database, abstract.
Oda et al., "Molecular Cloning and Characterization of a Novel Type of Histamine Receptor Preferentially Expressed in Leukocytes", *J. Biological Chem.*, vol. 275, No. 47, pp. 36781-36786 (2000).
Lovenberg et al., "Cloning and Functional Expression of the Human Histamine H3 Receptor", *Molecular Pharmacology*, vol. 55, pp. 1101-1107 (1999).
Raible et al., "Pharmacologic Characterization of a Novel Histamine Receptor on Human Eosinophils", *Am. J. Respiratory Critical Care Med.*, vol. 149, pp. 1506-1511 (1994).
West et al., "Identification of Two H3-Histamine Receptor Subtypes", *Molecular Pharmacology*, vol. 38, pp. 610-613 (1990).
Mikayama, "Molecular cloning and functional expression of a cDNA encoding glycosylation-inhibiting factor", *Proc. Natl. Acad. Sci.*, vol. 90, pp. 10056-10060 (1993).
Birre, "*Homo sapiens* chromosome 18 clone hRPK.178_F_map 18", Accession No. AC007922 (Jun. 26, 1999).

*Primary Examiner*—John D Ulm

(57) ABSTRACT

The present invention provides an isolated mammalian histamine receptor, isolated or recombinant nucleic acids and recombinant vectors encoding the same, host cells comprising the nucleic acids and vectors, and methods of making the receptor using the host cells. This invention further provides antibodies and antigen binding fragments thereof which specifically bind to the receptor and are useful for treating medical conditions caused or mediated by histamine. Also provided are screening methods for identifying specific agonists and antagonists of the mammalian histamine receptor.

2 Claims, No Drawings

SEQUENCE LISTING

```
<160> NUMBER OF SEQ ID NOS: 8

<210> SEQ ID NO 1
<211> LENGTH: 1173
<212> TYPE: DNA
<213> ORGANISM: Homo sapiens

<400> SEQUENCE: 1
atgccagata ctaatagcac aatcaattta tcactaagca ctcgtgttac tttagcattt      60
tttatgtcct tagtagcttt tgctataatg ctaggaaatg ctttggtcat tttagctttt     120
gtggtggaca aaaaccttag acatcgaagt agttattttt ttcttaactt ggccatctct     180
gacttctttg tgggtgtgat ctccattcct ttgtacatcc ctcacacgct gttcgaatgg     240
gattttggaa aggaaatctg tgtattttgg ctcactactg actatctgtt atgtacagca     300
tctgtatata acattgtcct catcagctat gatcgatacc tgtcagtctc aaatgctgtg     360
tcttatagaa ctcaacatac tggggtcttg aagattgtta ctctgatggt ggccgtttgg     420
gtgctggcct tcttagtgaa tgggccaatg attctagttt cagagtcttg gaaggatgaa     480
ggtagtgaat gtgaacctgg attttttcg gaatggtaca tccttgccat cacatcattc     540
ttggaattcg tgatcccagt catcttagtc gcttatttca acatgaatat ttattggagc     600
ctgtggaagc gtgatcatct cagtaggtgc caaagccatc ctggactgac tgctgtctct     660
tccaacatct gtggacactc attcagaggt agactatctt caaggagatc tctttctgca     720
tcgacagaag ttcctgcatc ctttcattca gagagacaga ggagaaagag tagtctcatg     780
ttttcctcaa gaaccaagat gaatagcaat acaattgctt ccaaaatggg ttccttctcc     840
caatcagatt ctgtagctct tcaccaaagg gaacatgttg aactgcttag agccaggaga     900
ttagccaagt cactggccat tctcttaggg gtttttgctg tttgctgggc tccatattct     960
ctgttcacaa ttgtcctttc attttattcc tcagcaacag gtcctaaatc agtttggtat    1020
agaattgcat tttggcttca gtggttcaat tcctttgtca atcctctttt gtatccattg    1080
tgtcacaagc gcttcaaaa ggctttcttg aaaatatttt gtataaaaaa gcaacctcta    1140
ccatcacaac acagtcggtc agtatcttct taa                                 1173

<210> SEQ ID NO 2
<211> LENGTH: 390
<212> TYPE: PRT
<213> ORGANISM: Homo sapiens

<400> SEQUENCE: 2

Met Pro Asp Thr Asn Ser Thr Ile Asn Leu Ser Leu Ser Thr Arg Val
 1               5                  10                  15

Thr Leu Ala Phe Phe Met Ser Leu Val Ala Phe Ala Ile Met Leu Gly
            20                  25                  30

Asn Ala Leu Val Ile Leu Ala Phe Val Val Asp Lys Asn Leu Arg His
        35                  40                  45
```

```
Arg Ser Ser Tyr Phe Phe Leu Asn Leu Ala Ile Ser Asp Phe Phe Val
        50                  55                  60

Gly Val Ile Ser Ile Pro Leu Tyr Ile Pro His Thr Leu Phe Glu Trp
 65                  70                  75                  80

Asp Phe Gly Lys Glu Ile Cys Val Phe Trp Leu Thr Thr Asp Tyr Leu
                 85                  90                  95

Leu Cys Thr Ala Ser Val Tyr Asn Ile Val Leu Ile Ser Tyr Asp Arg
                100                 105                 110

Tyr Leu Ser Val Ser Asn Ala Val Ser Tyr Arg Thr Gln His Thr Gly
            115                 120                 125

Val Leu Lys Ile Val Thr Leu Met Val Ala Val Trp Val Leu Ala Phe
130                 135                 140

Leu Val Asn Gly Pro Met Ile Leu Val Ser Glu Ser Trp Lys Asp Glu
145                 150                 155                 160

Gly Ser Glu Cys Glu Pro Gly Phe Phe Ser Trp Tyr Ile Leu Ala
                165                 170                 175

Ile Thr Ser Phe Leu Glu Phe Val Ile Pro Val Ile Leu Val Ala Tyr
                180                 185                 190

Phe Asn Met Asn Ile Tyr Trp Ser Leu Trp Lys Arg Asp His Leu Ser
            195                 200                 205

Arg Cys Gln Ser His Pro Gly Leu Thr Ala Val Ser Ser Asn Ile Cys
210                 215                 220

Gly His Ser Phe Arg Gly Arg Leu Ser Ser Arg Ser Leu Ser Ala
225                 230                 235                 240

Ser Thr Glu Val Pro Ala Ser Phe His Ser Glu Arg Gln Arg Lys
                245                 250                 255

Ser Ser Leu Met Phe Ser Ser Arg Thr Lys Met Asn Ser Asn Thr Ile
            260                 265                 270

Ala Ser Lys Met Gly Ser Phe Ser Gln Ser Asp Ser Val Ala Leu His
            275                 280                 285

Gln Arg Glu His Val Glu Leu Leu Arg Ala Arg Arg Leu Ala Lys Ser
290                 295                 300

Leu Ala Ile Leu Leu Gly Val Phe Ala Val Cys Trp Ala Pro Tyr Ser
305                 310                 315                 320

Leu Phe Thr Ile Val Leu Ser Phe Tyr Ser Ser Ala Thr Gly Pro Lys
                325                 330                 335

Ser Val Trp Tyr Arg Ile Ala Phe Trp Leu Gln Trp Phe Asn Ser Phe
            340                 345                 350

Val Asn Pro Leu Leu Tyr Pro Leu Cys His Lys Arg Phe Gln Lys Ala
            355                 360                 365

Phe Leu Lys Ile Phe Cys Ile Lys Lys Gln Pro Leu Pro Ser Gln His
            370                 375                 380

Ser Arg Ser Val Ser Ser
385                 390

<210> SEQ ID NO 3
<211> LENGTH: 2394
<212> TYPE: DNA
<213> ORGANISM: Homo sapiens

<400> SEQUENCE: 3 agacaattttt ctcacctctg taaattttag tctcaatctc acctaaatga atcagtctgc    60
cctttatctt gcccttttca ttctaccaac agatctgcac tttgaagtca atggtaaatt   120
actccagtga ataatagcag tataatatga cttgataata ttttgtaaa cttgtagtca   180
```

```
taatagtact atattcttct tagtcctcac ctcttccttg tctttagat cttaatttca      240 tgctgattac aaaaatccag ttttgttttc tttctatgtt ccatgcataa tacagtctta      300
agtgaatttc tctttttaa ttttatcgta atagaaactt atccagtttg aaaatcattc       360
cctaaagcat gcaataggaa aaagaacctc ctggctggga ctgcccaact ctgttctgat      420
cagtgggtgg gtgaggtagg gtttgagttg caagagcag ggaacgggca tgtgcccagg       480
tgagctcctg tgtgtgtcca gattttatat tcctaatccc agtaaggaag aaagcgtagt      540
gtgggagagg agagagctga tgactgcagt tctcaaaggt cctcagtgaa gttattttgg      600
aggccctggt ggtcacagga ttcagaaggc aagggatagg cagtggtcac caatggttga      660
aagtatggct tgtcccattt cttcctggtc ccttttct agcttcaaca tcagcttcct        720 ttttgagaa catatagaag aagaaggcta agagatggtg aagagactgc atgattaaac       780
tagatagacc tggtatacag tcactgaact tagtagatgt caataattat tattttaaa       840 aatttttatt tgttggccgg gcatggtggc tcacgcctga atcccagca ctttgggagg       900 ccaaggtggg cggatcatga ggtcaggaga tcgagaccat cctggccaac atggtgaaac      960
cccatctgta ctaaaataca aacaagtagc tggttgtggc gccgcatgcc tgtagtccca     1020
gctactcggg aggctgaggc aggggaattg cttgaacccg ggaggcggag tttgccagcc     1080
tggcaacaga acaagactct gtctaaaaag aaaaaaaat tttttttgttt aagacagcat     1140 cttgctctgt ctcccaggct ggagcgtagt aatgcaatca tagctcactg cagcctggaa     1200
ctccttggct caagcaatcc tgctgccttg gcctcccaag tatgtaggac tacaggtact     1260
cgccaccaca cctggataat taaaattatt tctgtagaga tgaagtctca ctgtgttgcc     1320
cagcctgggt gtcaataatt attttttaaa aaaattttt aaaaggttt ttgagacag       1380 attcttgctc tgtcacccag gctggagtgc agtagcatga tcagggatca ctgcaacctc     1440
tgcctcctgg gttcaagcga ttcttgtgcc taagccacct gagcagctgg gattacaggt     1500
gcatgccacc atgcctggct aatttttggta ttttagtag agatgaggtt ttgccatttt      1560
ggtcaggctg gaattttttt tttttaatt ttgataagac agggtattgc cgtgttggcc      1620
agactggtct caaactcctg ggctgaaaca atcctcccgc cttggcctcc caaagtgctg     1680
ggattatagg cacaagacac cacaataatt attgcctgta tgtcaattat tattttaaaa     1740
tattgttgta tttacttaat gtctttaatg catttgccca atattttaca ttgtactgct     1800
cagaggtatt cctttattat gtggttagca taggttatac ttttgctgac gattcacatt     1860
ttattagttt ggttatgttt tgtcctttta aaacattttc ttttgagatg gggtcttgct     1920
ctgttgccca cgcaggagtg cagtggcatg ctctcagctc actgcagccc tgactgctta     1980
ggctccagca atcttcttac gtcagcctcc agagtagctg ggaccgcagg cacttgccac     2040
cacgccccac taaaatttt ttaaattgtt gcctttcttg aagtgttctc tgcctgtctt     2100
tgtcacaaaa tttcatttt ctcatagtta atttcatctc tccggtaaga ttttattggt     2160
gtttctttta aactttgca gttccttacac cgtttggtga tttcatgtt tcttagaaac     2220 tttaaacctt taacttcaaa cattaaaata caagtctttt aagtacatga gtgcttagaa    2280
atgtacataa tgtttatata cacttatgcc ttacattaaa gtccaatatg agaaatacat     2340
gtttaacatt caataataat tttaaaaatt tgagaaataa actctcataa atgc           2394
```

<210> SEQ ID NO 4
<211> LENGTH: 21
<212> TYPE: DNA

```
<213> ORGANISM: Artificial Sequence
<220> FEATURE:
<223> OTHER INFORMATION: Description of Artificial Sequence: PCR primer
      sense strand

<400> SEQUENCE: 4
atgccagata ctaatagcac a                                              21

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: PCR primer
      antisense strand

<400> SEQUENCE: 5
cagaggtgag aaaattgtct ttaagaagat                                     30

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence: PCR primer
      sense strand

<400> SEQUENCE: 6
ctgtagctct tcaccaaagg gaa                                            23

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: PCR primer
      antisense strand

<400> SEQUENCE: 7
aaacccctaa gagaatggcc a                                              21

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Probe
      corresponding to 883-910 of SP9144 (labeled with
      fluorogenic probe FAM)

<400> SEQUENCE: 8
ctgcttagag ccaggagatt agccaagt                                       28
```

HISTAMINE RECEPTOR

This application is a continuation of U.S. application Ser. No. 10/616,088, filed Jul. 8, 2003, currently pending, which is a continuation of application Ser. No. 09/812,216, filed Mar. 19, 2001, now U.S. Pat. No. 6,613,533, which is a division of application Ser. No. 09/414,010, filed Oct. 7, 1999, now U.S. Pat. No. 6,204,017.

TECHNICAL FIELD

The present invention relates to mammalian histamine receptors. More particularly, it relates to human histamine receptors, isolated nucleic acids and recombinant vectors encoding the receptors, to methods of making the receptors, to methods of making fragments or fusion proteins of the receptors using recombinant DNA methodology or chemical synthesis, and to methods of using the receptors in screening systems to identify agonists and antagonists of the receptors useful for the treatment of various diseases.

BACKGROUND OF THE INVENTION

Histamines are implicated in a number of medical conditions, including inflammation, asthma, allergy, atopic dermatitis, stroke, myocardial infection, migraine, chronic obstructive pulmonary disease (COPD), rheumatoid arthritis, multiple sclerosis, inflammatory bowel disease, and psoriasis. Histamines regulate the intensity and duration of immune responses and are involved in cell-to-cell communication. Histamines are also involved in leukocyte migration and bronchovasoconstriction. As established by radioligand binding, physiological assays, and molecular cloning, different types of receptors for histamines exist. Furthermore, specific histamine receptor subtypes are involved in specific medical conditions such that drugs with subtype selectivity can be utilized to target individual medical conditions.

In view of the important role that histamines play in many physiological processes and medical conditions, there is a need for materials and methods useful for the identification of agonists and antagonists selective for the specific types of histamine receptors.

SUMMARY OF THE INVENTION

The present invention fills the foregoing need by providing such materials and methods. More particularly, this invention provides a novel mammalian histamine receptor, isolated nucleic acids or recombinant nucleic acids encoding the receptor, and recombinant vectors and host cells comprising such nucleic acids. The histamine receptor can be actively expressed in mammalian cells where it displays active ligand binding and positive intracellular signaling upon ligand activation. This novel receptor has high affinity for histamine. This invention further provides methods for the discovery of selective agonists and antagonists of the receptor that may be useful in the treatment and management of a variety of diseases including, for example, inflammation, asthma, and allergy, atopic dermatitis, stroke, myocardial infection, migraine, COPD, rheumatoid arthritis, multiple sclerosis, inflammatory bowel disease, and psoriasis.

The isolated or recombinant nucleic acids of the present invention are selected from the group consisting of:

(a) A nucleic acid encoding a polypeptide comprising an amino acid sequence defined by SEQ ID NO: 2 or a subsequence thereof;

(b) A nucleic acid that hybridizes under moderately stringent conditions to the nucleic acid of (a) and encodes a polypeptide that (i) binds histamine and (ii) is at least 80% identical to a receptor encoded by the nucleic acid of (a); and (c) A nucleic acid that, due to the degeneracy of the genetic code, encodes a mammalian histamine receptor encoded by a nucleic acid of (a) or (b).

This invention further provides methods of making a polypeptide comprising culturing a host cell comprising a nucleic acid encoding a mammalian histamine receptor comprising an amino acid sequence defined by SEQ ID NO: 2 or a subsequence thereof, under conditions in which the nucleic acid is expressed. In some embodiments, the method further comprises isolation of the polypeptide from the culture.

This invention also provides a recombinant nucleic acid comprising a sequence having at least about 70% identity over a stretch of at least about 30 nucleotides to the nucleic acid sequence of SEQ ID NO: 1, useful, e.g., as a probe or PCR primer for a related gene. Another embodiment further includes a polypeptide comprising at least about 60% identity over a stretch of at least about 20 amino acids to the amino acid sequence of SEQ ID NO: 2.

This invention also provides polypeptides comprising a fragment of a polypeptide having an amino acid sequence corresponding to the sequence of at least about 8 contiguous residues of the amino acid sequence of SEQ ID NO: 2. Preferably, the polypeptides comprise at least about 12, more preferably at least about 20, and most preferably at least about 30 such residues.

Still further, this invention provides fusion proteins comprising a polypeptide defined by SEQ ID NO: 2 or a fragment therefrom covalently linked to a fusion partner.

The present invention also provides antibodies, both polyclonal and monoclonal, that specifically bind to one or more of the histamine receptors or to polypeptides therefrom, and anti-idiotypic antibodies, both monoclonal and polyclonal, which specifically bind to the foregoing antibodies.

This invention further provides a method for producing a mammalian histamine receptor comprising culturing a host cell comprising a nucleic acid encoding a mammalian histamine receptor comprising an amino acid sequence defined by SEQ ID NO: 2 or a subsequence thereof, under conditions in which the nucleic acid is expressed. In one embodiment the receptor is isolated from the culture.

The present invention also provides a method for identifying a histamine agonist or antagonist comprising:

(a) Contacting a polypeptide having an amino acid sequence defined by SEQ ID NO: 2 or a subsequence thereof, in the presence of a known amount of labeled histamine or a surrogate thereof with a sample to be tested for the presence of a histamine agonist or antagonist; and (b) Measuring the amount of labeled histamine specifically bound to the receptor;

whereby a histamine agonist or antagonist in the sample is identified by measuring substantially reduced binding of the labeled histamine to the histamine receptor, compared to what would be measured in the absence of such agonist or antagonist.

In a preferred embodiment, membranes isolated from mammalian cells comprising a nucleic acid encoding the histamine receptor are used as the source of the receptor.

The present invention also provides a method for identifying an agonist or antagonist of a mammalian histamine receptor comprising:

(a) contacting cells expressing a polypeptide comprising an amino acid sequence defined by SEQ ID NO: 2 or a subsequence thereof, in the presence of a known amount of histamine or surrogate thereof with a sample to be tested for the presence of a mammalian histamine agonist or antagonist; and (b) measuring at least one cellular function modulated by the binding of a ligand to said receptor present in the cells;

whereby a mammalian histamine receptor agonist or antagonist in the sample is identified by measuring its effect on said cellular function compared to what would be measured in the absence of such agonist or antagonist.

Examples of cellular functions modulated by the binding of a ligand to a mammalian histamine receptor include: intracellular second messenger pathways activated via the histamine receptors (e.g., cyclicAMP, calcium, inositol phosphate and MAP kinase), changes in cell growth rate, secretion of hormones, receptor-stimulated $Ca^{2++}$ mobilization, mitogenic effects etc., This invention still further provides a method for treating histamine-mediated medical conditions comprising administering to a mammal afflicted with a medical condition caused or mediated by histamine, an effective amount of an agonist or antagonist of the histamine receptor that specifically binds to a mammalian histamine receptor having an amino acid sequence defined by SEQ ID NO: 2, or a subsequence thereof, and pharmaceutical compositions comprising one or more of such agonist or antagonist and a pharmaceutically acceptable carrier. Preferably, the mammal is a human being.

This invention also provides anti-sense oligonucleotides capable of specifically hybridizing to mRNA encoding a mammalian histamine receptor having an amino acid sequence defined by SEQ ID NO: 2 or a subsequence thereof so as to prevent translation of the mRNA. Additionally, this invention provides anti-sense oligonucleotides capable of specifically hybridizing to the genomic DNA molecule encoding a mammalian histamine receptor having an amino acid sequence defined by SEQ ID NO: 2 or a subsequence thereof.

This invention further provides a pharmaceutical composition comprising:

(a) An amount of an oligonucleotide effective to reduce activity of human histamine receptor by passing through a cell membrane and binding specifically with DNA or mRNA encoding human histamine receptor in the cell so as to prevent its transcription or translation; and (b) A pharmaceutically acceptable carrier capable of passing through a cell membrane. In an embodiment, the oligonucleotide is coupled to a substance that inactivates mRNA.

In another embodiment, the substance that inactivates mRNA is a ribozyme.

This invention also provides a method for measuring expression of a mammalian histamine receptor gene in a biological sample comprising the steps of:

(a) isolating messenger RNA from the sample;

(b) reverse transcribing the messenger RNA into cDNA;

(c) performing PCR on the cDNA using oligonucleotide primers derived from a nucleic acid defined by SEQ ID NO: 1; and (d) quantifying the amount of PCR product.

DESCRIPTION OF THE INVENTION

All references cited herein are hereby incorporated herein in their entirety by reference.

Histamine Receptor Characterization

The nucleotide sequence of the complete open reading frame and the corresponding amino acid sequence of the novel human histamine receptor of this invention are defined by SEQ ID NO: 1 and SEQ ID NO: 2, respectively. The cloned receptor resembles a member of the G-protein coupled receptor super-family that contains a 7-transmembrane domain. Furthermore, this receptor shares high homology at both the nucleotide and amino acid sequence levels with the previously described histamine receptors. The cloned receptor is able to bind ligands, for example, histamine, as demonstrated with radioligand saturation and competition assays. Histamine is also capable of activating the cloned receptor resulting in intracellular responses, as shown by measurement of intracellular $Ca^{2+}$ flux.

As used herein, the term "ligand" is defined to mean any molecule capable of specifically binding to the mammalian histamine receptors of the invention. Thus histamine itself is a ligand, as are agonists and antagonists that may compete with histamine for specific binding to the receptors.

The modifications that occur in a polypeptide often will be a function of how it is made. For polypeptides made by expressing a cloned gene in a host, for instance, the nature and extent of the modifications in large part will be determined by the host cell's post-translational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylating host, generally a eukaryotic cell. Insect cells often carry out the same post-translational glycosylations as mammalian cells do and, for this reason, insect cell expression systems have been developed to express efficiently mammalian proteins having the native patterns of glycosylation, inter alia. Similar considerations apply to other modifications.

It will be appreciated that the same type of modification may be present in the same or varying degrees at several sites in a given polypeptide. Also, a given polypeptide may contain many types of modifications.

The term "polypeptide" encompasses all such modifications, particularly those that are present in polypeptides synthesized by expressing a polynucleotide in a host cell.

"Variant(s)", as the term is used herein, are polynucleotides or polypeptides that differ from a reference polynucleotide or polypeptide respectively. Variants in this sense are described below and elsewhere in the present disclosure in greater detail. (1) A polynucleotide that differs in nucleotide sequence from another, reference polynucleotide. Changes in the nucleotide sequence of the variant may be silent, i.e. they may not alter the amino acids encoded by the polynucleotide. Where alterations are limited to silent changes of this type a variant will encode a polypeptide with the same amino acid sequence as the reference polypeptide. Changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below. (2) A polypeptide that differs in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination. (3) A variant may also be a fragment of a polynucleotide or polypeptide of the invention that differs from a reference polynucleotide or polypeptide sequence by being shorter than the reference sequence, such as by a terminal or internal deletion. A variant of a polypeptide of the invention also includes a polypeptide which retains essentially the same biological function or activity as such polypeptide, e.g., pro-proteins which can be activated by cleavage of the pro-protein portion to produce an active mature polypeptide. (4) A variant may also be (i) one in which one or more of the amino acid residues are substituted with a conserved or non-conserved amino acid residue (preferably a conserved amino acid residue) and such substituted amino acid residue may or may not be encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretory sequence or a sequence which is employed for purification of the mature polypeptide or a pro-protein sequence. (5) A variant of the polynucleotide or polypeptide may be a naturally occurring variant such as a naturally occurring allelic variant, or it may be a variant that is not known to occur naturally. Such non-naturally occurring variants or the polynucleotide may be made by mutagenesis techniques, including those applied to polynucleotides, cells or organisms, or may be made by recombinant means. Among polynucleotide variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions. All such variants defined above are deemed to be within the scope of those skilled in the art from the teachings herein and from the art.

The present invention also encompasses fragments, analogs and physical variants of the disclosed histamine receptor. As used herein, the term "polypeptide" or "peptide" means a fragment or segment, e.g., of a mammalian histamine receptor having an amino acid sequence defined by SEQ ID NO: 2 which comprises a subsequence of the complete amino acid sequence of the receptor containing at least about 8, preferably at least about 12, more preferably at least about 20, and most preferably at least about 30 or more contiguous amino acid residues, up to and including the total number of residues in the complete receptor.

The polypeptides of the invention can comprise any part of the complete sequence of such a receptor. Thus, although they could be produced by proteolytic cleavage of an intact receptor, they can also be made by chemical synthesis or by the application of recombinant DNA technology and are not limited to polypeptides delineated by proteolytic cleavage sites. The polypeptides, either alone or cross-linked or conjugated to a carrier molecule to render them more immunogenic, are useful as antigens to elicit the production of antibodies. The antibodies can be used, e.g., in immunoassays of the intact receptors, for immunoaffinity purification, etc.

The term "analog(s)" means a mammalian histamine receptor of the invention which has been modified by deletion, addition, modification or substitution of one or more amino acid residues in the wild-type receptor. It encompasses allelic and polymorphic variants, and also muteins and fusion proteins which comprise all or a significant part of such a mammalian histamine receptor, e.g., covalently linked via a side-chain group or terminal residue to a different protein, polypeptide or moiety (fusion partner).

Some amino acid substitutions are preferably "conservative", with residues replaced with physically or chemically similar residues, such as Gly/Ala, Asp/Glu, Val/Ile/Leu, Lys/Arg, Asn/Gln and Phe/Trp/Tyr. Analogs having such conservative substitutions typically retain substantial histamine binding activity. Other analogs, which have non-conservative substitutions such as AsniGlu, Val/Tyr and His/Glu, may substantially lack such activity, Nevertheless, such analogs are useful because they can be used as antigens to elicit production of antibodies in an immunologically competent host. Because these analogs retain many of the epitopes (antigenic determinants) of the wild-type receptors from which they are derived, many antibodies produced against them can also bind to the active-conformation or denatured wild-type receptors. Accordingly, such antibodies can also be used, e.g., for the immunopurification or immunoassay of the wild-type receptors.

Some analogs are truncated variants in which residues have been successively deleted from the amino- and/or carboxyl-termini, while substantially retaining the characteristic ligand binding activity.

Modifications of amino acid residues may include but are not limited to aliphatic esters or amides of the carboxyl terminus or of residues containing carboxyl side chains, O-acyl derivatives of hydroxyl group-containing residues, and N-acyl derivatives of the amino-terminal amino acid or amino-group containing residues, e.g., lysine or arginine.

Other analogs are mammalian histamine receptors containing modifications, such as incorporation of unnatural amino acid residues, or phosphorylated amino acid residues such as phosphotyrosine, phosphoserine or phosphothreonine residues. Other potential modifications include sulfonation, biotinylation, or the addition of other moieties, particularly those that have molecular shapes similar to phosphate groups.

Analogs of the mammalian histamine receptors can be prepared by chemical synthesis or by using site-directed mutagenesis [Gillman et at., *Gene* 8:81 (1979); Roberts et al., *Nature,* 328:731 (1987) or Innis (Ed.), 1990, *PCR Protocols. A Guide to Methods and Applications*, Academic Press, New York, N.Y.] or the polymerase chain reaction method [PCR; Saiki et at, *Science* 239:487 (1988)], as exemplified by Daugherty et al. [*Nucleic Acids Res.* 19:2471 (1991)] to modify nucleic acids encoding the complete receptors. Adding epitope tags for purification or detection of recombinant products is envisioned.

General techniques for nucleic acid manipulation and expression that can be used to make the analogs are described generally, e.g., in Sambrook, et al., *Molecular Cloning: A Laboratory Manual* (2d ed.), 1989, Vols. 1-3, Cold Spring Harbor Laboratory. Techniques for the synthesis of polypeptides are described, for example, in Merrifield, *J. Amer. Chem. Soc.* 85:2149 (1963); Merrifield, *Science* 232:341 (1986); and Atherton et al., *Solid Phase Peptide Synthesis: A Practical Approach,* 1989, IRL Press, Oxford.

Still other analogs are prepared by the use of agents known in the art for their usefulness in cross-linking proteins through reactive side groups. Preferred derivatization sites with cross-linking agents are free amino groups, carbohydrate moieties and cysteine residues.

Substantial retention of ligand binding activity by the foregoing analogs of the mammalian histamine receptors typically entails retention of at least about 50%, preferably at least about 75%, more preferably at least about 80%, and most preferably at least about 90% of the histamine binding activity and/or specificity of the corresponding wild-type receptor.

Nucleic Acids and Expression Vectors

As used herein, the term "isolated nucleic acid" means a nucleic acid such as an RNA or DNA molecule, or a mixed polymer, which is substantially separated from other components that are normally found in cells or in recombinant DNA expression systems. These components include but are not limited to ribosomes, polymerases, serum components, and flanking genomic sequences. The term thus embraces a nucleic acid that has been removed from its naturally occurring environment, and includes recombinant or cloned DNA isolates and chemically synthesized analogs or analogs biologically synthesized by heterologous systems. A substantially pure molecule includes isolated forms of the molecule.

An isolated nucleic acid will generally be a homogeneous composition of molecules but may, in some embodiments, contain minor heterogeneity. Such heterogeneity is typically found at the ends of nucleic acid coding sequences or in regions not critical to a desired biological function or activity.

A "recombinant nucleic acid" is defined either by its method of production or structure. Some recombinant nucleic acids are thus made by the use of recombinant DNA techniques which involve human intervention, either in manipulation or selection. Others are made by fusing two fragments that are not naturally contiguous to each other. Engineered vectors are encompassed, as well as nucleic acids comprising sequences derived using any synthetic oligonucleotide process.

For example, a wild-type codon may be replaced with a redundant codon encoding the same amino acid residue or a conservative substitution, while at the same time introducing or removing a nucleic acid sequence recognition site. Similarly, nucleic acid segments encoding desired functions may be fused to generate a single genetic entity encoding a desired combination of functions not found together in nature. Although restriction enzyme recognition sites are often the targets of such artificial manipulations, other site-specific targets, e.g., promoters, DNA replication sites, regulation sequences, control sequences, or other useful features may be incorporated by design. Sequences encoding epitope tags for detection or purification as described above may also be incorporated.

A nucleic acid "fragment" is defined herein as a nucleotide sequence comprising at least about 17, generally at least about 25, preferably at least about 35, more preferably at least about 45, and most preferably at least about 55 or more contiguous nucleotides.

This invention further encompasses recombinant DNA molecules and fragments having sequences that are identical or highly homologous to those described herein. The nucleic acids of the invention may be operably linked to DNA segments that control transcription, translation, and DNA replication.

"Identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Similarity" between two polypeptides is determined by comparing the amino acid sequence and its conserved amino acid substitutes of one polypeptide to the sequence of a second polypeptide. "Identity" and "similarity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Printer*, Gribskov, M. and Devereux, J., eds., M Stockton Press, New York, 1991; and Carillo, H., and Lipman, D., SIAM *J. Applied Math.*, 48.1073 (1988). Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., *Nucleic Acids Research* 12 (1):387 (1984)), BestFit, BLASTP, BLASTN, and FASTA (Altschul, S. F. et al., *J. Mol. Biol.* 215:403-410 (1990). The BLAST X program is publicly available from NCBI and other sources (*BLAST Manual*, Altschul, S., et al., NCBI NLM NIH Bethesda, Md. 20894; Altschul, S., et al., *J. Mol Biol.* 215:403-410 (1990). The well-known Smith Waterman algorithm may also be used to determine identity.

Preferred parameters for polypeptide sequence comparison include the following:

1) Algorithm: Needleman and Wunsch, *J. Mol. Biol.* 48:443-453 (1970)

Comparison matrix: BLOSSUM62 from Hentikoff and Hentikoff, *Proc Natl. Acad. Sci. USA.* 89:10915-10919 (1992)

Gap Penalty: 12

Gap Length Penalty: 4

A program useful with these parameters is publicly available as the "gap" program from Genetics Computer Group, located in Madison, Wis. The aforementioned parameters are the default parameters for peptide comparisons (along with no penalty for end gaps).

Preferred parameters for polynucleotide comparison include the following:

1) Algorithm: Needleman and Wunsch, *J. Mol. Biol.* 48:443-453 (1970)

Comparison matrix: matches=+10, mismatch=0

Gap Penalty, 50

Gap Length Penalty: 3

Available as the Gap program from Genetics Computer Group, located in Madison, Wis. Given above are the default parameters for nucleic acid comparisons.

Preferred polynucleotide embodiments further include an isolated polynucleotide comprising a polynucleotide sequence having at least a 50, 60, 70, 80, 85, 90, 95, 97 or 100% identity to the reference sequence of SEQ ID NO: 1, wherein said polynucleotide sequence may be identical to the reference sequence of SEQ ID NO: 1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NO: 1 by the integer defining the percent identity divided by 100 and then subtracting that product from said total number of nucleotides in SEQ ID NO: 1, or: $n_n x_n - (x_n y)$, wherein $n_n$ is the number of nucleotide alterations, $x_n$ is the number of nucleotides in SEQ ID NO: 1, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO: 2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO: 2, that is it may be 100% identical, or it may include up to a certain integer number of amino acid alterations as compared to the reference sequence such that the percent identity is less than 100% identity. Such alterations are selected form the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of amino acids in SEQ ID NO: 2 by the integer defining the percent identity divided by 100 and then subtracting that product from said total number of amino acids in SEQ ID NO: 2, or $n_n = x_n - (x_n \, y)$, wherein $n_n$ is the number of amino acid alterations, $x_n$ is the total number of amino acids in SEQ ID NO: 2, y is, for instance 0.70 for 70%, 0.80 for 80%, 0.85 for 85% etc., is the symbol for the multiplication operator, and wherein any non-integer product of $x_n$ and y is rounded down to the nearest integer prior to subtracting it from $x_n$.

Preferred polypeptide embodiments further include an isolated polypeptide comprising a polypeptide having at least a 50, 60, 70, 80, 85, 90, 95, 97 or 100% identity to a polypeptide reference sequence of SEQ ID NO: 2, wherein said polypeptide sequence may be identical to the reference sequence of SEQ ID NO: 2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino-or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO: 2 by the integer defining the percent identity divided by 100 and then subtraction that product from said total number of amino acids in SEQ ID NO: 2, or: $n_a \, x_a - (x_a \, y)$, wherein $n_a$ is the number of amino acid alterations, $x_a$ is the total number of amino acids in SEQ ID NO: 2, y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO: 2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino-or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO: 2 by the integer defining the percent identity divided by 100 and then subtracting that product from said total number of amino acids in SEQ ID NO: 2, or $n_a = x_a \, (x_a \, y)$, wherein $n_a$ is the number of amino acid alterations, $x_a$ is the total number of amino acids in SEQ ID NO: 2, y is, for instance 0.70 for 70%, 0.80 for 80%, 0.85 for 85% etc., and is the symbol for the multiplication operator, and wherein any non-integer product of $x_a$ and y is rounded down to the nearest integer prior to subtracting it from $x_a$.

The term "homology", as it is used herein, embraces both identity and similarity.

Some of the physical variants have substantial amino acid sequence homology with the amino acid sequences of the mammalian histamine receptors or polypeptides. In this invention, amino acid sequence homology, or sequence identity is determined by optimizing residue matches and, if necessary, by introducing gaps as required. Homologous amino acid sequences are typically intended to include natural allelic, polymorphic and interspecies variations in each respective sequence.

Typical homologous proteins or peptides will have from 25-100% homology (if gaps can be introduced) to 50-100% homology (if conservative substitutions are included), with the amino acid sequence of the histamine receptors. Primate species receptors are of particular interest.

Observed homologies will typically be at least about 35%, preferably at least about 50%, more preferably at least about 75%, and most preferably at least about 80% or more. See Needleham et al., J. Mol. Biol. 48:443-453 (1970); Sankoff et al. in Time Warps, String Edits, and Macromolecules: The Theory and Practice of Sequence Comparison, 1983, Addison-Wesley, Reading, Mass; and software packages from IntelliGenetics, Mountain View, Calif, and the University of Wisconsin Genetics Computer Group, Madison, Wis.

Glycosylation variants include, e.g., analogs made by modifying glycosylation patterns during synthesis and processing in various alternative eukaryotic host expression systems, or during further processing steps. Particularly preferred methods for producing glycosylation modifications include exposing the mammalian histamine receptors to glycosylating enzymes derived from cells that normally carry out such processing, such as mammalian glycosylation enzymes. Alternatively, deglycosylation enzymes can be used to remove carbohydrates attached during production in eukaryotic expression systems.

"Homologous nucleic acid sequences" are those which when aligned and compared exhibit significant similarities. Standards for homology in nucleic acids are either measures for homology generally used in the art by sequence comparison or based upon hybridization conditions, which are described in greater detail below.

Substantial nucleotide sequence homology is observed when there is identity in nucleotide residues in two sequences (or in their complementary strands) when optimally aligned to account for nucleotide insertions or deletions, in at least about 50%, preferably in at least about 75%, more preferably in at least about 90%, and most preferably in at least about 95% of the aligned nucleotides.

Substantial homology also exists when one sequence will hybridize under selective hybridization conditions to another. Typically, selective hybridization will occur when there is at least about 55% homology over a stretch of at least about 30 nucleotides, preferably at least about 65% over a stretch of at least about 25 nucleotides, more preferably at least about 75%, and most preferably at least about 90% over about 20 nucleotides. See, e.g., Kanehisa, *Nucleic Acids Res.* 12.203 (1984).

The lengths of such homology comparisons may encompass longer stretches and in certain embodiments may cover a sequence of at least about 17, preferably at least about 25, more preferably at least about 50, and most preferably at least about 75 nucleotide residues.

Stringency of conditions employed in hybridizations to establish homology are dependent upon factors such as salt concentration, temperature, the presence of organic solvents, and other parameters. Stringent temperature conditions usually include temperatures in excess of about 30° C., often in excess of about 37° C., typically in excess of about 45° C., preferably in excess of about 55° C., more preferably in excess of about 65° C., and most preferably in excess of about 70° C. Stringent salt conditions will ordinarily be less than about 1000 mM, usually less than about 500 mM, more usually less than about 400 mM, preferably less than about 300 mM, more preferably less than about 200 mM, and most preferably less than about 150 mM. For example, salt concentrations of 100, 50 and 20 mM are used. The combination of the foregoing parameters, however, is more important than the measure of any single parameter. See, e.g., Wetmur et al., *J. Mol. Biol.* 31:349 (1968).

A further indication that two nucleic acid sequences of polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions Another indication that two nucleic acid sequences are substantially identical is that the two molecules hybridize to each other under stringent conditions, as described below.

The term "substantially pure" is defined herein to mean a mammalian histamine receptor, nucleic acid or other material that is free from other contaminating proteins, nucleic acids, and other biologicals derived from an original source organism or recombinant DNA expression system. Purity may be assayed by standard methods and will typically exceed at least about 50%, preferably at least about 75%, more preferably at least about 90%, and most preferably at least about 95% purity. Purity evaluation may be made on a mass or molar basis.

Nucleic acids encoding the histamine receptors or fragments thereof can be prepared by standard methods. For example, DNA can be chemically synthesized using, e.g., the phosphoramidite solid support method of Matteucci et al. [*J. Am. Chem. Soc.* 103:3185 (1981)], the method of Yoo et al. [*J. Biol. Chem.* 764:17078 (1989)], or other well known methods. This can be done by sequentially linking a series of oligonucleotide cassettes comprising pairs of synthetic oligonucleotides, as described below.

Of course, due to the degeneracy of the genetic code, many different nucleotide sequences can encode the histamine receptors. The codons can be selected for optimal expression in prokaryotic or eukaryotic systems. Such degenerate variants are of course also encompassed by this invention.

Moreover, nucleic acids encoding the histamine receptors can readily be modified by nucleotide substitutions, nucleotide deletions, nucleotide insertions, and inversions of nucleotide stretches. Such modifications result in novel DNA sequences that encode antigens having immunogenic or antigenic activity in common with the wild-type receptors. These modified sequences can be used to produce wild type or mutant receptors, or to enhance expression in a recombinant DNA system.

Insertion of the DNAs encoding the histamine receptors into a vector is easily accomplished when the termini of both the DNAs and the vector comprise compatible restriction sites. If this cannot be done, it may be necessary to modify the termini of the DNAs and/or vector by digesting back single-stranded DNA overhangs generated by restriction endonuclease cleavage to produce blunt ends, or to achieve the same result by filling in the single-stranded termini with an appropriate DNA polymerase.

Alternatively, desired sites may be produced, e.g., by ligating nucleotide sequences (linkers) onto the termini. Such linkers may comprise specific oligonucleotide sequences that define desired restriction sites. Restriction sites can also be generated by the use of the polymerase chain reaction (PCR). See, e.g., Saiki et a., *Science* 239:487 (1988). The cleaved vector and the DNA fragments may also be modified if required by homopolymeric tailing.

Recombinant expression vectors used in this invention are typically self-replicating DNA or RNA constructs comprising nucleic acids encoding one of the mammalian histamine receptors, usually operably linked to suitable genetic control elements that are capable of regulating expression of the nucleic acids in compatible host cells. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and sequences that terminate transcription and translation. Expression vectors also may contain an origin of replication that allows the vector to replicate independently of the host cell.

Vectors that could be used in this invention include microbial plasmids, viruses, bacteriophage, integratable DNA fragments, and other vehicles that may facilitate integration of the nucleic acids into the genome of the host. Plasmids are the most commonly used form of vector but all other forms of vectors which serve an equivalent function and which are, or become, known in the art are suitable for use herein. See, e.g., Pouwels et al., *Cloning Vectors. A Laboratory Manual,* 1985 and Supplements, Elsevier, N.Y., and Rodriguez et al. (eds.), *Vectors: A Survey of Molecular Cloning Vectors and Their Uses,* 1988, Buttersworth, Boston, Mass.

Expression of nucleic acids encoding the histamine receptors of this invention can be carried out by conventional methods in either prokaryotic or eukaryotic cells. Although strains of *E. coli* are employed most frequently in prokaryotic systems, many other bacteria such as various strains of *Pseudomonas* and *Bacillus* are know in the art and can be used as well.

Prokaryotic expression control sequences typically used include promoters, including those derived from the β-lactamase and lactose promoter systems [Chang et al., *Nature,* 198:1056 (1977)], the tryptophan (trp) promoter system [Goeddel et al., *Nucleic Acids Res.* 8:4057 (1980)], the lambda $P_L$ promoter system [Shimatake et al., *Nature,* 292:

128 (1981)] and the tac promoter [De Boer et at, *Proc. Natl. Acad. Sci. USA* 292:128 (1983)]. Numerous expression vectors containing such control sequences are known in the art and available commercially.

Suitable host cells for expressing nucleic acids encoding the mammalian histamine receptors include prokaryotes and higher eukaryotes. Prokaryotes include both gram negative and positive organisms, e.g., *E. coli* and *B. subtilis*. Higher eukaryotes include established tissue culture cell lines from animal cells, both of non-mammalian origin, e.g., insect cells, and birds, and of mammalian origin, e.g., human, primates, and rodents.

Prokaryotic host-vector systems include a wide variety of vectors for many different species. As used herein, *E. coli* and its vectors will be used generically to include equivalent vectors used in other prokaryotes. A representative vector for amplifying DNA is pBR322 or many of its derivatives. Vectors that can be used to express the mammalian histamine receptors include but are not limited to those containing the lac promoter (pUC-series); trp promoter (pBR322-trp); Ipp promoter (the pIN-series); lambda-pP or pR promoters (pOTS); or hybrid promoters such as ptac pDR540). See Brosius et al., "Expression Vectors Employing Lambda-, trp-, lac-, and Ipp-derived Promoters", in Rodriguez and Denhardt (eds.) *Vectors: A Survey of Molecular Cloning Vectors and Their Uses*, 1988, Buttersworth, Boston, pp. 205-236.

Higher eukaryotic tissue culture cells are preferred hosts for the recombinant production of the mammalian histamine receptors. Although any higher eukaryotic tissue culture cell line might be used, including insect baculovirus expression systems, mammalian cells are preferred. Transformation or transfection and propagation of such cells have become a routine procedure. Examples of useful cell lines include HeLa cells, Chinese hamster ovary (CHO) cell lines, baby rat kidney (BRK) cell lines, insect cell lines, bird cell lines, and monkey (COS) cell lines.

Expression vectors for such cell lines usually include an origin of replication, a promoter, a translation initiation site, RNA splice sites (if genomic DNA is used), a polyadenylation site, and a transcription termination site. These vectors also usually contain a selection gene or amplification gene. Suitable expression vectors may be plasmids, viruses, or retroviruses carrying promoters derived, e.g., from such sources as adenovirus, SV40, parvoviruses, vaccinia virus, or cytomegalovirus. Representative examples of suitable expression vectors include pCR® 3.1, pCDNA1, pCD [Okayama et al., *Mol. Cell Biol.* 5:1136 (1985)], pMC1neo Poly-A [Thomas et al., *Cell* 51:503(1987)], pUC19, pREP8, pSVSPORT and derivatives thereof, and baculovirus vectors such as pAC 373 or pAC 610.

Protein Purification

The proteins, polypeptides and antigenic fragments of this invention can be purified by standard methods, including but not limited to salt or alcohol precipitation, preparative disc-gel electrophoresis, isoelectric focusing, high pressure liquid chromatography (HPLC), reversed-phase HPLC, gel filtration, cation and anion exchange and partition chromatography, and countercurrent distribution. Such purification methods are well known in the art and are disclosed, e.g., in *Guide to Protein Purification, Methods in Enzymology*, Vol, 182, M. Deutscher, Ed., 1990, Academic Press, New York, N.Y. More specific methods applicable to purification of the histamine receptors are described below.

Purification steps can be followed by carrying out assays for ligand binding activity as described below. Particularly where a receptor is being isolated from a cellular or tissue source, it is preferable to include one or more inhibitors of proteolytic enzymes is the assay system, such as phenylmethanesulfonyl fluoride (PMSF).

Screening Systems and Methods

The invention allows the discovery of selective agonists and antagonists of the novel receptor that may be useful in treatment and management of a variety of diseases including inflammation, asthma, allergy, atopic dermatitis, stroke, myocardial infection, migraine, COPD, rheumatoid arthritis, multiple sclerosis, inflammatory bowel disease, and psoriasis. Thus, the histamine receptor of this invention can be employed in screening systems to identify agonists or antagonists of the receptor. Essentially, these systems provide methods for bringing together a mammalian histamine receptor, an appropriate known ligand, including histamine itself, and a sample to be tested for the presence of a histamine agonist or antagonist.

Two basic types of screening systems can be used, a labeled-ligand binding assay and a "functional" assay. A labeled ligand for use in the binding assay can be obtained by labeling histamine or a known histamine agonist or antagonist with a measurable group as described above in connection with the labeling of antibodies. Various labeled forms of histamine are available commercially or can be generated using standard techniques. In an example below, $^3$H-histamine is used as the ligand.

Typically, a given amount of the histamine receptor of the invention is contacted with increasing amounts of a labeled ligand, such as labeled histamine itself, and the amount of the bound labeled ligand is measured after removing unbound labeled ligand by washing. As the amount of the labeled ligand is increased, a point is eventually reached at which all receptor binding sites are occupied or saturated. Specific receptor binding of the labeled ligand is abolished by a large excess of unlabeled ligand.

Preferably, an assay system is used in which non-specific binding of the labeled ligand to the receptor is minimal. Non-specific binding is typically less than 50%, preferably less than 15%, and more preferably less than 10% of the total binding of the labeled ligand.

As used herein, the term "histamine ligand" is defined to mean histamine itself or an analog of histamine, and extending up to the complete histamine molecule. For regulatory purposes it may be desirable to use histamine or an active fragment thereof as the histamine ligand in conjunction with the human receptor when screening for histamine agonists or antagonists for human therapeutic purposes.

In principle, a binding assay of the invention could be carried out using a soluble receptor of the invention, e.g., following production and refolding by standard methods from an *E. coli* expression system, and the resulting receptor-labeled ligand complex could be precipitated, e.g., using an antibody against the receptor. The precipitate could then be washed and the amount of the bound labeled ligand could be measured.

Preferably, however, a nucleic acid encoding one of the histamine receptors of the invention is transfected into an appropriate host cell, whereby the receptor will become incorporated into the membrane of the cell. A membrane fraction can then be isolated from the cell and used as a source of the receptor for assay. Preferably, specific binding of the labeled ligand to a membrane fraction from the untransfected host cell will be negligible.

The binding assays of this invention can be used to identify both histamine agonists and antagonists, because both will interfere with the binding of the labeled ligand to the receptor.

In the basic binding assay, the method for identifying a histamine agonist or antagonist comprises:

(a) contacting a mammalian histamine receptor having an amino acid sequence defined by SEQ ID NO: 2 or a subsequence thereof, in the presence of a known amount of labeled histamine with a sample to be tested for the presence of a histamine agonist or antagonist; and (b) measuring the amount of labeled histamine bound to the receptor;

whereby a histamine agonist or antagonist in the sample is identified by measuring substantially reduced binding of the labeled histamine to the histamine receptor, compared to what would be measured in the absence of such agonist or antagonist.

Preferably, the histamine receptor used to identify a histamine agonist or antagonist for human therapeutic purposes has an amino acid sequence defined by SEQ ID NO: 2 or a subsequence thereof.

In one embodiment of the invention, the foregoing method further comprises:

(c) Contacting a mammalian histamine receptor in the presence of a known amount of labeled histamine with a compound identified as a histamine agonist or antagonist in steps (a) and (b); and (d) Measuring the amount of labeled histamine bound to the receptor; whereby a histamine agonist or antagonist specific for the histamine receptor is identified by measuring substantially undiminished binding of the labeled histamine to the receptor, compared to what would be measured in the absence of such agonist or antagonist.

Determination of whether a particular molecule inhibiting binding of the labeled ligand to the receptor is an antagonist or an agonist is then determined in a second, functional assay. The functionality of histamine agonists and antagonists identified in the binding assay can be determined in cellular and animal models.

Functional Assays for Antagonists/Agonists of Histamine Receptors

In cellular models, parameters for intracellular activities mediated by histamine receptors can be monitored for antagonistic and/or agonistic activities. Such parameters include but are not limited to intracellular second messenger pathways activated via the histamine receptors, changes in cell growth rate, secretion of hormones, etc., using published methods. Examples of such methods are, measurement of the effects of the ligands on receptor-mediated inhibition of forskolin-stimulated intracellular cAMP production [Parker et at, *Mol. Brain Res.* 34:179-189 (1995)], receptor-stimulated $Ca^{2++}$ mobilization and mitogenic effects [Sethi et al., *Cancer Res.* 51:1674-1679 (1991)], and inositol phosphate production and MAP kinase induction (Wang et at, *Biochemistry* 37:6711-17 (1998). The FLIPR method described in this invention is also suitable for measuring intracellular release of calcium.

Agonists of histamine receptors may also be identified directly by using functional assays. An agonist may or may not directly inhibit histamine binding to histamine receptors.

In addition to the methods described above, activities of an antagonist may be measured in cellular models for altered intracellular cAMP or $Ca^{2-}$ concentrations. Histamine-induced chemotaxis using cultured cells can also be utilized. Furthermore, models employing *Xenopus laevis*, pigment dispersion/aggregation in melanophores, and aequorin assay in mammalian cells are suitable for this purpose. Methods using animals or animal tissues for such activities can also be employed. Histamine-stimulated neutrophil chemotaxis, enhanced neutrophil-endothelial interaction, neutrophil activation leading to degranulation and release of mediators, enzymes and superoxides, inflammatory pain, and increased cytokine production and transcription are examples of such methods.

Other Mammalian Histamine Receptors

The present invention provides methods for cloning mammalian histamine receptors from other mammalian species. Briefly, Southern and Northern blot analysis can be carried out to identify cells from other species expressing genes encoding the histamine receptors. Complementary DNA (cDNA) libraries can be prepared by standard methods from mRNA isolated from such cells, and degenerate probes or PCR primers based on the nucleic acid and amino acid sequences provided herein can be used to identify clones encoding a histamine receptor.

Alternatively, expression cloning methodology can be used to identify particular clones encoding a histamine receptor. An antibody preparation which exhibits cross-reactivity with histamine receptors from a number of mammalian species may be useful in monitoring expression cloning.

However identified, clones encoding histamine receptors from various mammalian species can be isolated and sequenced, and the coding regions can be excised and inserted into an appropriate vector.

Other Related Genes

The present invention also provides compositions and methods for cloning other genes related to the gene encoding a polypeptide defined by SEQ ID NO: 2. Specifically, this invention provides a recombinant nucleic acid comprising a sequence having at least about 70% identity over a stretch of at least about 30 nucleotides to the nucleic acid sequence of SEQ ID NO: 1, useful, e.g., as a probe or PCR primer for a related gene.

Localization of mRNA Encoding the Polypeptide of SEQ ID NO: 2

The present invention also provides compositions and methods for localization of messenger RNA coding for the polypeptide defined by the amino acid sequence of SEQ ID NO: 2.

Specifically, human multiple tissue and cancer cell line blots containing approximately 2 µg of poly(A)$^+$ RNA per lane, are purchased from Clontech (Palo Alto, Calif.). Probes are radiolabeled with [$\alpha^{32}$P] dATP, e.g., using the Amersham Rediprime random primer labeling kit (RPN1633). Prehybridization and hybridizations are performed at 65° C. in 0.5M $Na_2HPO_4$, 7% SDS, 0.5M EDTA (pH 8.0). High stringency washes are conducted, e.g., at 65° C. with two initial washes in 2×SSC, 0.1% SDS for 40 min followed by a subsequent wash in 0.1×SSC, 0.1% SDS for 20 min. Membranes are then exposed at −70° C. to X-Ray film (Kodak) in the presence of intensifying screens. More detailed studies by cDNA library Southerns are performed with selected clones of nucleic acids having the nucleotide sequence defined by SEQ ID NO: 1 to examine their expression in other cell subsets.

Two prediction algorithms that take advantage of the patterns of conservation and variation in multiply aligned sequences, (Rost and Sander (1994) *Proteins* 19:55-72) and DSC (King and Stemberg (1996) *Protein Sci.* 5:2298-2310), are used.

Alternatively, two appropriate primers are selected and RT-PCR is used on an appropriate mRNA sample selected for the presence of message to produce a cDNA, e.g., a sample which expresses the gene.

Full length clones may be isolated by hybridization of cDNA libraries from appropriate tissues pre-selected by PCR signal.

Message for genes encoding a polypeptide having the amino acid sequence of SEQ ID NO: 2 are assayed by appropriate technology, e.g., PCR, immunoassay, hybridization, or otherwise. Tissue and organ cDNA preparations are available, e.g., from Clontech, Mountain View, Calif.

Southern Analysis on cDNA libraries are performed as follows: DNA (5 µg) from a primary amplified cDNA library is digested with appropriate restriction enzymes to release the inserts, run on a 1% agarose gel and transferred to a nylon membrane (Schleicher and Schuell, Keene, N.H.).

Samples for human mRNA isolation and distribution of expression may include: fresh peripheral blood eosinophils and eosinophils unstimulated or stimulated overnight with interleukin-5; peripheral blood neutrophils and neutrophils unstimulated or stimulated with lipopolysaccharide; cultured primary bronchial epithelial cells; peripheral blood CD4$^+$ T cells polarized to Th2 cells using anti-CD3 and anti-CD28 monoclonal antibodies, IL-4 and anti-interferon gamma antibody for 12, 13 or 20 days; peripheral blood CD4$^+$ T cells polarized to Th1 cells using anti-CD3 and anti-CD28 monoclonal antibodies, anti-IL-4 monoclonal antibody and IL-12 for 6 or 13 days; and a T cell clone, B21, nonactivated or activated with anti-CD3 monoclonal antibody overnight.

Samples from cDNA libraries from human mRNA isolation may include: peripheral blood mononuclear cells (monocytes, T cells, NK cells, granulocytes, B cells), resting (T100); peripheral blood mononuclear cells, activated with anti-CD3 for 2, 6, 12 h pooled (T101); T cell, TH0 clone Mot 72, resting (T102); T cell, TH0 clone Mot72, activated with anti-CD28 and anti-CD3 for 3, 6, 12 h pooled (T103); T cell,TH0 clone Mot 72, anergic treated with specific peptide for 2, 7, 12 h pooled (T104); T cell, TH1 clone HY06, resting (T107); T cell, TH1 clone HY06, activated with anti-CD28 and anti-CD3 for 3, 6, 12 h pooled (T108); T cell, TH1 clone HY06, anergic treated with specific peptide for 2, 6, 12 h pooled (T109); T cell, TH2 clone HY935, resting (T110); T cell, TH2 clone HY935, activated with anti-CD28 and anti-CD3 for 2, 7, 12 h pooled (T111) T cell, TH2 clone B21, resting (T114); T cell, TH2 B21 activated with anti-CD3 for 5 h (T115); T cell, random gamma delta T cell clones, resting (T119); T cell, Jurkat, resting (T120); T cell, Jurkat, activated with PMA and ionomycin for 1, 6 hr pooled (T122); T cell line, CD28-, nonactivated (T123); T cell, TR-1 regulatory cell line (T124); splenocytes, resting (B100); splenocytes, activated with anti-CD40 and IL-4 (B101); B cell EBV lines pooled WT49, RSB, JY, CVIR, 721.221, RM3, HSY, resting (B102); B cell line JY, activated with PMA and ionomycin for 1, 6 h pooled (B103); natural killer (NK) 20 clones pooled, resting (K100); NK 20 clones pooled, activated with PMA and ionomycin for 6 h (K101); NK clone, NKA6, activated with PMA and ionomycin for 6 h (K102); NKL clone, derived from peripheral blood of LGL leukemia patient, IL-2 treated (K106); NK cytotoxic clone 640-A30-1, resting (K107); NK clone, non-cytotoxic variant of clone 640-A230-1, resting (K108); hematopoietic precursor line TF1, activated with PMA and ionomycin for 1, 6 h pooled (C100); U937 premonocytic line, resting (M100); U937 premonocytic line, activated with PMA and ionomycin for 1, 6 h pooled (M101); elutriated monocytes, activated with LPS, IFN-γ, anti-IL-10 for 1, 2, 6, 12, 24 h pooled (M102); elutriated monocytes, activated with LPS, IFN-γ, IL-10 for 1, 2, 6, 12, 24 h pooled (M103); elutriated monocytes, activated with LPS, IFN-γ, anti-IL-10 for 4, 16 h pooled (M106); elutriated monocytes, activated with LPS, IFN-γ, IL-10 for 4, 16 h pooled (M107); elutriated monocytes, activated LPS for 1 h (M108); elutriated monocytes, activated LPS for 6 h (M109); primary mast cells (C114); dendritic cells (DC) 70% CD1a+, from CD34+ GM-CSF, TNF-α 12 days, resting (D101); DC 70% CD1a+, from CD34+ GM-CSF, TNF-α 12 days, activated with PMA and ionomycin for 1 hr (D102); DC 70% CD1a+, from CD34+ GM-CSF, TNF-α 12 days, activated with PMA and ionomycin for 6 hr (D103); DC 95% CD1a+, from CD34+ GM-CSF, TNF-α 12 days FACS sorted, activated with PMA and ionomycin for 1, 6 h pooled (D104); DC 95% CD14+, from CD34+ GM-CSF, TNF-α 12 days FACS sorted, activated with PMA and ionomycin 1, 6 hr pooled (D105); DC CD1a+ CD86+, from CD34+ GM-CSF, TNF-α 12 days FACS sorted, activated with PMA and ionomycin for 1, 6 h pooled (D106); DC from monocytes after 5 days in GM-CSF, IL-4, resting (D108); DC from monocytes after 5 days in GM-CSF, IL-4, activated LPS 4, 16 h pooled (D109); DC from monocytes after 5 days in GM-CSF, IL-4, activated TNF-α, monocyte supernatant for 4, 16 h pooled (D110); DC from monocytes after 7 days in GM-CSF, IL-4, resting (D111); DC from monocytes after 7 days in GM-CSF, IL-4, activated by CD40L (D112); DC from CD34+ stem cells after 12 days in GM-CSF, TNF-α and TGF-β, resting (D113); DC from CD34+ stem cells after 12 days in GM-CSF, TNF-α and TGF-β, activated with TNF-α/TGF-β (D114); lung fibroblast sarcoma line MRC5, activated with PMA and ionomycin for 1, 6 h pooled (C101); kidney epithelial carcinoma cell line CHA, activated with PMA and ionomycin for 1, 6 h pooled (C102); A549 epithelial cell line, resting (C109); A549 epithelial cell line, activated with IL1-β 2, 6, 24 hr and pooled (C110); kidney fetal 28 wk male (O100); lung fetal 28 wk male (O101); liver fetal 28 wk male (O102); heart fetal 28 wk male (O103); brain fetal 28 wk male (O104); small intestine fetal 28 wk male (O107); adipose tissue fetal 28 wk male (O108); ovary fetal 25 wk female (O109); uterus fetal 25 wk female (O110); testes fetal 28 wk male (O111); spleen fetal 28 wk male (O112); adult placenta 28 wk (O113); and tonsil inflamed, from 12 year old (X100); total lung, asthmatic (X114, X117); colon, Crohn's patient (X113, X115, X116).

Antibody Production

Antigenic (i.e., immunogenic) fragments of the mammalian histamine receptors of this invention, which may or may not have ligand binding activity, may be produced. Regardless of whether they bind histamine, such fragments, like the complete receptors, are useful as antigens for preparing antibodies by standard methods that can bind to the complete receptors. Shorter fragments can be concatenated or attached to a carrier. Because it is well known in the art that epitopes generally contain at least about five, preferably at least about 8, amino acid residues [Ohno et al., *Proc. Natl. Acad. Sci. USA* 82.2945 (1985)], fragments used for the production of antibodies will generally be at least that size. Preferably, they will contain even more residues, as described above. Whether a given fragment is immunogenic can readily be determined by routine experimentation.

Although it is generally not necessary when complete mammalian histamine receptors are used as antigens to elicit antibody production in an immunologically competent host, smaller antigenic fragments are preferably first rendered more immunogenic by cross-linking or concatenation, or by coupling to an immunogenic carrier molecule (i.e., a macromolecule having the property of independently eliciting an immunological response in a host animal). Cross-linking or conjugation to a carrier molecule may be required because small polypeptide fragments sometimes act as haptens (molecules which are capable of specifically binding to an antibody but incapable of eliciting antibody production, i.e., they are not immunogenic). Conjugation of such fragments to an immunogenic carrier molecule renders them more immunogenic through what is commonly known as the "carrier effect".

Suitable carrier molecules include, e.g., proteins and natural or synthetic polymeric compounds such as polypeptides, polysaccharides, lipopolysaccharides etc.

Protein carrier molecules are especially preferred, including but not limited to keyhole limpet hemocyanin and mammalian serum proteins such as human or bovine gamma-globulin, human, bovine or rabbit serum albumin, or methylated or other derivatives of such proteins. Other protein carriers will be apparent to those skilled in the art. Preferably, but not necessarily, the protein carrier will be foreign to the host animal in which antibodies against the fragments are to be elicited.

Covalent coupling to the carrier molecule can be achieved using methods well known in the art, the exact choice of which will be dictated by the nature of the carrier molecule used. When the immunogenic carrier molecule is a protein, the fragments of the invention can be coupled, e.g., using water-soluble carbodiimides such as dicyclohexylcarbodiimide or glutaraldehyde.

Coupling agents such as these can also be used to cross-link the fragments to themselves without the use of a separate carrier molecule. Such cross-linking into aggregates can also increase immunogenicity. Immunogenicity can also be increased by the use of known adjuvants, alone or in combination with coupling or aggregation.

Suitable adjuvants for the vaccination of animals include but are not limited to Adjuvant 65 (containing peanut oil, mannide monooleate and aluminum monostearate); Freund's complete or incomplete adjuvant; mineral gels such as aluminum hydroxide, aluminum phosphate and alum; surfactants such as hexadecylamine, octadecylamine, lysolecithin, dimethyldioctadecylammonium bromide, N,N-dioctadecyl-N',N'-bis(2-hydroxymethyl) propanediamine, methoxyhexadecylglycerol and pluronic polyols; polyanions such as pyran, dextran sulfate, poly IC, polyacrylic acid and carbopol; peptides such as muramyl dipeptide, dimethylglycine and tuftsin; and oil emulsions. The polypeptides could also be administered following incorporation into liposomes or other microcarriers.

Information concerning adjuvants and various aspects of immunoassays are disclosed, e.g., in the series by P. Tijssen, *Practice and Theory of Enzynze Immunoassays*, 3rd Edition, 1987, Elsevier, N.Y. Other useful references covering methods for preparing polyclonal antisera include *Microbiology*, 1969, Hoeber Medical Division, Harper and Row; Landsteiner, *Specificity of Serological Reactions*, 1962, Dover Publications, New York, and Williams, et al., *Methods in Immunology and Immunochemistry*, Vol. 1, 1967, Academic Press, New York.

Serum produced from animals immunized using standard methods can be used directly, or the IgG fraction can be separated from the serum using standard methods such as plasmaphoresis or adsorption chromatography with IgG-specific adsorbents such as immobilized Protein A. Alternatively, monoclonal antibodies can be prepared.

Hybridomas producing monoclonal antibodies against the histamine receptors of the invention or antigenic fragments thereof are produced by well-known techniques. Usually, the process involves the fusion of an immortalizing cell line with a B-lymphocyte that produces the desired antibody. Alternatively, non-fusion techniques for generating immortal antibody-producing cell lines can be used, e.g., virally-induced transformation [Casali et al., *Science* 234:476 (1986)]. Immortalizing cell lines are usually transformed mammalian cells, particularly myeloma cells of rodent, bovine, and human origin. Most frequently, rat or mouse myeloma cell lines are employed as a matter of convenience and availability.

Techniques for obtaining antibody-producing lymphocytes from mammals injected with antigens are well known. Generally, peripheral blood lymphocytes (PBLs) are used if cells of human origin are employed, or spleen or lymph node cells are used from non-human mammalian sources. A host animal is injected with repeated dosages of the purified antigen (human cells are sensitized in vitro), and the animal is permitted to generate the desired antibody-producing cells before they are harvested for fusion with the immortalizing cell line. Techniques for fusion are also well known in the art, and in general involve mixing the cells with a fusing agent, such as polyethylene glycol.

Hybridomas are selected by standard procedures, such as HAT (hypoxanthine-aminopterin-thymidine) selection. Those secreting the desired antibody are selected using standard immunoassays, such as Western blotting, ELISA (enzyme-linked immunosorbent assay), RIA (radioimmunoassay), or the like. Antibodies are recovered from the medium using standard protein purification techniques [Tijssen, *Practice and Theory of Enzyme Immunoassays* (Elsevier, Amsterdam, 1985)].

Many references are available to provide guidance in applying the above techniques [Kohler et al., *Hybridoma Techniques* (Cold Spring Harbor Laboratory, New York, 1980); Tijssen, *Practice and Theory of Enzyme Immunoassays* (Elsevier, Amsterdam, 1985); Campbell, *Monoclonal Antibody Technology* (Elsevier, Amsterdam, 1984); Hurrell, *Monoclonal Hybridoma Antibodies: Techniques and Applications* (CRC Press, Boca Raton, Fla., 1982)]. Monoclonal antibodies can also be produced using well-known phage library systems. See, e.g., Huse, et al., *Science* 246:1275 (1989); Ward, et al., *Nature,* 341:544 (1989).

Antibodies thus produced, whether polyclonal or monoclonal, can be used, e.g., in an immobilized form bound to a solid support by well known methods, to purify the receptors by immunoaffinity chromatography.

Antibodies against the antigenic fragments can also be used, unlabeled or labeled by standard methods, as the basis for immunoassays of the mammalian histamine receptors. The particular label used will depend upon the type of immunoassay. Examples of labels that can be used include but are not limited to radiolabels such as $^{32}P$, $^{125}I$, $^{3}H$ and $^{14}C$; fluorescent labels such as fluorescein and its derivatives, rhodamine and its derivatives, dansyl and umbelliferone; chemiluminescers such as luciferia and 2,3-dihydrophthalazinediones; and enzymes such as horseradish peroxidase, alkaline phosphatase, lysozyme and glucose-6-phosphate dehydrogenase.

The antibodies can be tagged with such labels by known methods. For example, coupling agents such as aldehydes, carbodiimides, dimaleimide, imidates, succinimides, bisdiazotized benzadine and the like may be used to tag the antibodies with fluorescent, chemiluminescent or enzyme labels. The general methods involved are well known in the art and are described, e.g., in *Immunoassay: A Practical Guide,* 1987, Chan (Ed.), Academic Press, Inc., Orlando, Fla. Such immunoassays could be carried out, for example, on fractions obtained during purification of the receptors.

The antibodies of the present invention can also be used to identify particular cDNA clones expressing the histamine receptors in expression cloning systems.

Neutralizing antibodies specific for the ligand-binding site of a receptor can also be used as antagonists (inhibitors) to block histamine binding. Such neutralizing antibodies can readily be identified through routine experimentation, e.g., by using the radioligand binding assay described infra. Antagonism of histamine activity can be accomplished using complete antibody molecules, or well-known antigen binding fragments such as Fab, Fc, F(ab)$_2$, and Fv fragments.

Definitions of such fragments can be found, e.g., in Klein, *Immunology* (John Wiley, New York, 1982); Parham, Chapter 14, in Weir, ed. *Immunochemistry*, 4th Ed. (Blackwell Scientific Publishers, Oxford, 1986). The use and generation of antibody fragments has also been described, e.g.: Fab fragments [Tijssen, *Practice and Theory of Enzyme Immunoassays* (Elsevier, Amsterdam, 1985)], Fv fragments [Hochman et al., Biochemistry 12:1130 (1973); Sharon et al., Biochemistry 15:1591 (1976); Ehrlich et al., U.S. Pat. No. 4,355,023] and antibody half molecules (Auditore-Hargreaves, U.S. Pat. No. 4,470,925). Methods for making recombinant Fv fragments based on known antibody heavy and light chain variable region sequences have further been described, e.g., by Moore et al. (U.S. Pat. No. 4,642,334) and by Plückthun [*Bio/Technology* 9:545 (1991)]. Alternatively, they can be chemically synthesized by standard methods.

Anti-idiotypic antibodies, both polyclonal and monoclonal, can also be produced using the antibodies elicited against the receptors as antigens. Such antibodies can be useful as they may mimic the receptors.

Pharmaceutical Compositions

The histamine receptor agonists and antagonists of this invention can be used therapeutically to stimulate or block the activity of histamine, and thereby to treat any medical condition caused or mediated by histamine. The dosage regimen involved in a therapeutic application will be determined by the attending physician, considering various factors which may modify the action of the therapeutic substance, e.g., the condition, body weight, sex and diet of the patient, the severity of any infection, time of administration, and other clinical factors.

Typical protocols for the therapeutic administration of such substances are well known in the art. Administration of the compositions of this invention is typically by parenteral, by intraperitoneal, intravenous, subcutaneous, or intramuscular injection, or by infusion or by any other acceptable systemic method. Often, treatment dosages are titrated upward from a low level to optimize safety and efficacy. Generally, daily dosages will fall within a range of about 0.01 to 20 mg protein per kilogram of body weight. Typically, the dosage range will be from about 0.1 to 5 mg per kilogram of body weight.

Dosages will be adjusted to account for the smaller molecular sizes and possibly decreased half-lives (clearance times) following administration. It will be appreciated by those skilled in the art, however, tat the histamine antagonists of the invention encompass neutralizing antibodies or binding fragments thereof in addition to other types of inhibitors, including small organic molecules and inhibitory ligand analogs, which can be identified using the methods of the invention.

An "effective amount" of a composition of the invention is an amount that will ameliorate one or more of the well-known parameters that characterize medical conditions caused or mediated by histamine.

Although the compositions of this invention could be administered in simple solution, they are more typically used in combination with other materials such as carriers, preferably pharmaceutical carriers. Useful pharmaceutical carriers can be any compatible, non-toxic substances suitable for delivering the compositions of the invention to a patient. Sterile water, alcohol, fats, waxes, and inert solids may be included in a carrier. Pharmaceutically acceptable adjuvants (buffering agents, dispersing agents) may also be incorporated into the pharmaceutical composition. Generally, compositions useful for parenteral administration of such drugs are well known; e.g. *Remington's Pharmaceutical Science*, 17th Ed. (Mack Publishing Company, Easton, Pa., 1990). Alternatively, compositions of the invention may be introduced into a patient's body by implantable drug delivery systems [Urquhart et al., *Ann. Rev. Pharmacol Toxicol.* 24:199 (1984)].

Therapeutic formulations may be administered in many conventional dosage formulation. Formulations typically comprise at least one active ingredient, together with one or more pharmaceutically acceptable carriers. Formulations may include those suitable for oral, rectal, nasal, or parenteral (including subcutaneous, intramuscular, intravenous and intradermal) administration.

The formulations may conveniently be presented in unit dosage form and may be prepared by any methods well known in the art of pharmacy. See, e.g., Gilman et al. (eds.) (1990), *The Pharmacological Bases of Therapeutics*, 8th Ed., Pergamon Press; and *Remington's Pharmaceutical Sciences*, supra, Easton, Pa.; Avis et al. (eds.) (1993) *Pharmaceutical Dosage Forms: Parenteral Medications* Dekker, N.Y.; Lieberman et al. (eds.) (1990) *Pharmaceutical Dosage Forms: Tablets* Dekker, N.Y.; and Lieberman et al. (eds.) (1990), *Pharmaceutical Dosage Forms: Disperse Systems* Dekker, N.Y.

The present invention also encompasses anti-idiotypic antibodies, both polyclonal and monoclonal, which are produced using the above-described antibodies as antigens. These antibodies are useful because they may mimic the structures of the receptors.

Anti-Sense Molecules

The present invention also encompasses anti-sense oligonucleotides capable of specifically hybridizing to mRNA encoding a mammalian histamine receptor having an amino acid sequence defined by SEQ ID NO: 2 or a subsequence thereof so as to prevent translation of the mRNA. Additionally, this invention contemplates anti-sense oligonucleotides capable of specifically hybridizing to the genomic DNA molecule encoding a mammalian histamine receptor having an amino acid sequence defined by SEQ ID NO: 2 or a subsequence thereof.

This invention further provides pharmaceutical compositions comprising (a) an amount of an oligonucleotide effective to reduce activity of human histamine receptor by passing through a cell membrane and binding specifically with mRNA encoding human histamine receptor in the cell so as to prevent its translation and (b) a pharmaceutically acceptable carrier capable of passing through a cell membrane. In an embodiment, the oligonucleotide is coupled to a substance that inactivates mRNA. In another embodiment, the substance that inactivates mRNA is a ribozyme.

EXAMPLES

The present invention can be illustrated by the following examples. Unless otherwise indicated, percentages given below for solids in solid mixtures, liquids in liquids, and solids in liquids are on a wt/wt, vol/vol and wt/vol basis, respectively. Sterile conditions were generally maintained during cell culture.

Materials and General Methods

Human marathon-ready cDNAs and RACE kit were from Clontech. Oligonucleotides were custom-synthesized by Gibco Life Technologies. 293-EBNA cell line was obtained from Invitrogen, Histamines and other ligands were purchased from Sigma Chemicals. Radioligands were from NEN.

Standard methods were used, as described, e.g., in Maniatis et al., *Molecular Cloning: A Laboratory Manual* 1982, Cold Spring Harbor Laboratory, Cold Spring Harbor Press; Sambrook et al., *Molecular Cloning: A Laboratory Manual*, (2d ed.), Vols 1-3, 1989, Cold Spring Harbor Press, NY; Ausubel et al., *Biology*, Greene Publishing Associates, Brooklyn N.Y.; or Ausubel, et al. (1987 and Supplements), *Current Protocols in Molecular Biology*, Greene/Wiley, New York; Innis et al. (eds.) *PCR Protocols: A Guide to Methods and Applications*, 1990, Academic Press, N.Y.

Example 1

Cloning and Characterization of the Human Histamine Receptor

The amino acid sequences of known G-protein coupled receptors (GPCRs) were used to conduct a BLAST search of nucleotide databases. The search identified a 200 nucleotide sequence as being a putative GPCR, with homology to the $6^{th}$ transmembrane domain of the 5HT1B receptor. The corresponding cDNA clone was obtained and sequenced further to reveal the $6^{th}$ and $7^{th}$ transmembrane domains.

Searching of public sequence databases with the cDNA clone identified identical sequence on a fragment of chomosome 18 deposited in Genbank. Analysis of this chromosomal fragment identified several discontinuous sequences which when translated exhibited characteristics of GPCRs. Comparison of the predicted amino acid sequence of this assemblage with known GPCRs revealed the highest homology to the H3 histamine receptor. A putative ATG translation initiation codon was identified in this sequence, as well as a putative downstream stop codon (originally identified in the cDNA sequence).

Specific sense and antisense oligonucleotide primers were synthesized beginning with the initiating ATG and covering the stop codon. The sequence of the primers are: Oligo 9144-5', atgccagatactaatagcaca (SEQ ID NO: 4); Oligo 9144-3', cagaggtgagaaaattgtctttaagaagat (SEQ ID NO: 5). These primers were used for PCR with cDNA prepared from eosinophil mRNA by reverse transcriptase. PCR thermal cycling conditions used were: 35 cycles of 95° C., 30 sec.; 62° C., 30 sec.; 68° C., 2 min. A single band at 1.2 kb was detected from this reaction. This band was cloned into the vector pCR3.1 (Invitrogen) to form the expression construct pCR3.1-SP9144. Sequencing of the insert in pCR3.1-SP9144 identified a single open reading frame of 1,173 nucleotides (SEQ ID NO: 1), designated SP9144, encoding a predicted protein sequence of 390 amino acids (SEQ ID NO: 2).

Hydrophobicity analysis of the predicted 390aa protein indicates the presence of 7 hydrophobic domains, putative transmembrane regions, a feature common to G-protein coupled receptors. BLAST analysis with this protein sequence revealed homology to known GPCRs with the highest degree of similarity to the H3 histamine receptor. Sequence alignment analysis using the Clustal method showed 34% identity overal between SP9144 and the H3 histamine receptor and 58% within the predicted transmembrane regions. These analyses suggest that the protein encoded by the SP9144 ORF may be a receptor for histamine Example 2

Ligand Identification and Agonist/Antagonist Screening Assay:

HEK-293-EBNA cells (Invitrogen) were grown in DMEM/10% FBS until 70-80% confluent and used for transfection with LipofectAmine2000 reagent (Life Technologies) using 8 μg pCR3.1-SP9144 DNA/75 cm² flask. In certain experiments, DNA constructs encoding chimeric G-protein alpha subunits (Gqi5) (Conklin et al., *Nature*, 363:274-276 (1993)) were cotransfected with pCR-SP9144. 24 hours after transfection, cells were harvested and plated at 25,000 cells/well in clear bottom, black walled 96 well plates precoated with poly-D-lysine (Beckton-Dickenson) and cultured overnight in DMEM/10% FBS. For the assay, growth media was removed and replaced with 50 μl /well dye loading medium containing DMEM, 10% FBS, 20 mM HEPES pH 7.4, 2.5 mM probenecid (Sigma), 1 mM Fluo3-AM (Sigma) (dissolved in 10% pluronic acid in DMSO). After 1 hr. at 37° C., the cell plates were washed 4 times with 250 μl Hanks Balanced Salt Solution (HBSS) lacking phenol red and containing 20 mM HEPES, 2.5 mM probenecid, and 0.1% BSA (wash buffer). A final volume of 100 μl/well of wash buffer was added to the plates, and the plates were placed into a Fluorescent Imaging Plate Reader (FLIPR, Molecular Devices) equilibrated to 37° C. In the FLIPR, changes in intracellular [Ca$^{++}$] levels were measured by excitation of Fluo3 fluorescence at 488 nm while fluorescence output was monitored at 500-560 nm. Fluorescence was monitored once per second for 1 minute, and every 6 seconds for 2 minutes thereafter. After a 10 sec baseline measurement was established, drugs at 3× final concentration (1×10$^{-4}$ M to 1×10$^{-9}$ M) were added in a volume of 50 μl while the fluorescence continued to be monitored. Values extracted for data analysis represented the maximal fluorescence value minus the minimal fluorescence value detected following the drug addition. Drug stock solutions were initially dissolved in water (or DMSO) and diluted to 3× final concentration using wash buffer.

Examination of the activity of naturally occurring biogenic amine neurotransmitters indicated that SP9144 was specifically activated by histamine, and not by other biogenic amines such as dopamine, epinephrine, nor-epinephrine or serotonin. Furthermore this activation by histamine is specific to SP9144 and is not observed in mock transfected cells. Histamine analogs are also able to activate SP9144 with a rank order of potency Histamine>Nα-methylhistamine>(R) α-methylhistamine>>(S)α-methylhistamine (inactive). Other compounds selective for H3 histamine receptors are also able to activate SP9144, albeit with reduced efficacy. The rank order of potency is clobenpropit>imetit>impromidine>buramimide. In contrast, no activation of SP9144 by the H3 antagonist thioperimide was observed, however, the activation by (R)α-methylhistamine could be blocked in a dose dependent manner by thioperimide. The H1 and H2 selective antagonists, chlorphenirimine and cimetidine, were completely inactive at SP9144.

Example 3

Histamine Binding Assay

Membrane preparation: HEK-293 cells transfected with SP9144 as described above were harvested by incubating in 5 mM EDTA/phosphate-buffered saline followed by repeated pipetting. The cells were centrifuged 5 min at 1000×g. The EDTA/PBS was decanted and an equal volume of ice-cold 50 mM Tris-HCl, pH 7.5, was added and cells were broken up with a Polytron (PT10tip, setting 5, 30 sec). Nuclei and unbroken cells were sedimented at 1000×g for 10 min and then the supernatant was centrifuged at 50,000×g for 10 min. The supernatant was decanted, the pellet was resuspended by Polytron, a sample was taken for protein assay (bicinchoninic acid, Pierce), and the tissue was again centrifuged at 50,000×g. Pellets were stored frozen at −20° C.

Binding assay: For saturation binding, four concentrations of [$^3$H]histamine (15 Ci/mmol,Dupont NEN) were incubated without and with $10^{-5}$ M histamine in triplicate with 50 µg of membrane protein in a total volume of 200 µl of 50 mM Tris-HCl, pH 7.5, for 30 min at 30° C. Samples were filtered on GF/B filters and washed thrice with 2 ml of cold Tris buffer. Filters were dried in a microwave oven, impregnated with Meltilex wax scintillant, and counted at 45% efficiency. For competition binding assays, five concentrations of compounds were incubated in triplicate with 18 nM [$^3$H]histamine and 70 µg of membrane protein under the conditions described above. Curves were fit to the data with Prism (GraphPad Software) nonlinear least-squares curve-fitting program and Ki values were derived from IC50 values according to Cheng and Prusoff(Cheng, Y. C., and Prusoff, W. H. (1973) Relationship between the inhibition constant (Ki) and the concentration of inhibitor which causes 50 percent inhibition (IC50) of an enzymatic reaction. *Biochem. Pharmacol.* 22, 3099-3108).

[$^3$H]-Histamine bound specifically to membranes from HEK-293 cells transfected with SP9144 DNA, but not to membranes from untransfected HEK-293 cells. The $K_d$ for histamine binding determined by saturation analysis was 10 nM. [$^3$H]-Histamine binding could be blocked by both histamine analogs and other histaminergic compounds with the following rank order of potency: imetit>clobenpropit>histamine>impromidine>Na-methylhistamine>burimamide>(R)-a-methylhistamine>thioperimide>>(S)-a-methylhistamine. Chlorphenirimine and cimetidine were not able to block [$^3$H]-histamine binding at concentrations of 10 µM.

Example 4 mRNA Cell/Tissue Distribution

Total cellular RNA was isolated from cells by one of two standard methods: 1) guanidine isothiocyanate/Cesium chloride density gradient centrifugation (Maniatis et al., Molecular Cloning: A Laboratory Manual, 1982, Cold Spring Harbor Laboratory, Cold Spring Harbor Press); or with the Tri-Reagent protocol according to the manufacturer's specifications (Molecular Research Center, Inc., Cincinatti, Ohio). Total RNA prepared by the Tri-reagent protocol was treated with DNAse I to remove genomic DNA contamination. For library construction, Poly A+ mRNA was selected using Oligotex kit from Qiagen (Santa Clarita, Calif.) according to the manufacturer's specifications. Libraries were constructed using standard methods (Maniatis et al., Molecular Cloning: A Laboratory Manual, 1982, Cold Spring Harbor Laboratory, Cold Spring Harbor Press).

For relative quantitation of the mRNA distribution of SP9144, total RNA from each cell or tissue source was first reverse transcribed. Two µg of total RNA was reverse transcribed using 25 pmole random hexamer primers and 100 pmole poly dT$_{15}$ (Boehlringer Mannheim, Indianapolis, Ind.), 0.5 mM each of dATP, dCTP, dGTP and dTTP (Pharmacia, Uppsala, Sweden), 5 mM DTT, 1 µl RNAsin (Promega, Madison Wis.) in a final volume of 20 µl. The first strand synthesis buffer and Superscript II (1 µl/20 µl) reverse transcriptase were from Gibco/BRL (Gaithersburg, Md.). Replicate samples were also prepared similarly with the exception that no Superscript II reverse transcriptase was added; these samples serve as controls for genomic contamination. The reaction was incubated at 42-45° C. for 90 minutes, heated to 95° C. for 5 min and cooled on ice. The volume was adjusted to 200 µl with Tris HCl pH 7.4, yielding a final concentration of 10 ng/µl of starting RNA.

For relative quantitation of the distribution of SP9144 mRNA in cells and tissues the Perkin Elmer ABI Prism® 7700 Sequence Detection system was used according to the manufacturer's specifications and protocols. Multiplex PCR reactions were set up to quantitate SP9144 and the housekeeping gene HPRT, according to ABI 7700 Sequence Detection System User Bulletin #2. For HPRT primers and VIC™-labelled probe, the PE kit 4310890E was used. Forward and reverse primers and probe for SP9144 were designed using the Perkin Elmer ABI Primer Express™ software and were synthesized by PE Biosystems (Foster City, Calif.). The SP9144 forward primer sequence was: CTGTAGCTCT-TCACCAAAGGGAA (SEQ ID NO: 6) corresponding to positions 851 to 873. The SP9144 reverse primer sequence was AAACCCCTAAGAGAATGGCCA (SEQ ID NO: 7) corresponding to positions 924 to 945. The fluorogenic probe, labelled with FAM as the reporter dye, is CTGCTTAGAGC-CAGGAGATTAGCCAAGT (SEQ ID NO: 8) corresponding to positions 883 to 910. The following reactions in a final volume of 50 µl were set up in duplicate for each cDNA (RNA) sample (where the final concentrations of each component are indicated): 1× TaqMan buffer A, 5.5 mM MgCl2, 200 nM each of dATP, dCTP, dGTP and dUTP, 0.025 U/µl AmpliTaq Gold™, 0.01 U/µl AmpErase UNG®, HPRT forward, reverse primers and probe 1×, SP9144 forward and reverse primers each at 200 nM, 100 nM SP9144 FAM-labelled probe, and 20 ng of template cDNA (from cells and tissue or 40 ng from libraries). Thermal cycling parameters were 2 min HOLD at 50° C., 10 min HOLD at 95° C., followed by melting at 95° C. for 15 sec and annealing/extending at 60° C. for 1 min for each of 40 cycles.

Relative quantitation of the SP9144 mRNA levels was done using the comparative $C_T$ method described in the ABI 7700 Sequence Detection System User Bulletin #2 for multiplex reactions. Following derivation of the ΔRn value, representing the normalized reporter signal for each gene (SP9144 and HPRT) minus the baseline signal for each gene established in the first few cycles of PCR, $C_T$ (threshold cycle) values, representing the first PCR cycle at which an increase in reporter fluorescence signal above baseline is detected, were determined for each gene. For each sample the SP9144 values were normalized to that of HPRT in the same sample according to :Δ $C_T$ SP9144 minus Δ$C_T$ HPRT. The relative level of expression of SP9144 is expressed as $2^{(-\Delta CT)}$. Duplicate values were then averaged.

No significant signal above background was detected except very low (+), low (++) medium (+++) and high (++++) in the cell-derived and library samples. Very low (+) expression was observed in fetal testes, Crohn's colon, asthmatic lung, epithelial cells and resting and activated CD4$^+$ Th1 cells. Low expression (++) was observed in elutriated monocytes, activated with LPS, IFN-γ, anti-IL-10 for 4, 16 h; mast cells; dendritic cells (DC) 70% CD1a+, from CD34+ GM-CSF, TNF-α 12 days, resting; DC from monocytes after 5 days in GM-CSF, IL-4, resting; DC from monocytes after 5 days in GM-CSF, IL-4, activated TNF-α, monocyte supernatant for 4, 16 h pooled; DC from monocytes after 7 days in GM-CSF, IL-4, activated by CD40L; and in DC from CD34+ stem cells after 12 days in GM-CSF, TNT-α and TGF-β, activated with TNF-α/TGF-β. Medium expression (+++) was observed in activated polarized (day 12, 13, 20) CD4+ Th2 cells. High expression (++++) was observed in unstimulated and IL-5 stimulated eosinophils and unstimulated or LPS stimulated neutrophils.

Many modifications and variations of this invention can be made without departing from its spirit and scope, as will be apparent to those skilled in the art. The specific embodiments described herein are offered by way of example only, and the invention is to be limited only by the terms of the appended claims, together with the full scope of equivalents to which such claims are entitled.

What is claimed is:

1. A method for identifying an agonist or antagonist of a mammalian histamine receptor, comprising:
   (a) contacting a polypeptide comprising the amino acid sequence defined by SEQ ID NO: 2 or a histamine binding fragment thereof in the presence of a known amount of labeled histamine or a surrogate thereof with a sample to be tested for the presence of a histamine agonist or antagonist;
   (b) measuring the amount of labeled histamine or surrogate thereof specifically bound to the polypeptide;
   (c) contacting cells expressing a polypeptide comprising the amino acid sequence defined by SEQ ID NO: 2 or a histamine binding fragment thereof with said sample; and
   (d) measuring at least one cellular function modulated by the binding of a ligand to a polypeptide comprising the amino acid sequence defined by SEQ ID NO: 2;
   whereby a histamine agonist in the sample is identified by measuring:
   (i) substantially reduced binding of the labeled histamine or surrogate thereof to the polypeptide compared to what would be measured in the absence of said sample in step (b); and (ii) substantially increased level of said cellular function compared to what would be measured in the absence of said sample in step (d);

and whereby a histamine antagonist in the sample is identified by measuring:

(i) substantially reduced binding of the labeled histamine or surrogate thereof to the polypeptide compared to what would be measured in the absence of said sample in step (b); and (ii) substantially similar or reduced level of said cellular function compared to what would be measured in the absence of said sample in step (d).

2. The method of claim 1, wherein said at least one cellular function is selected from the group consisting of:

(a) inhibition of forskolin-stimulated intracellular cAMP production;
(b) $Ca^{2+}$ mobilization;
(c) inositol phosphate production; and
(d) intracellular release of calcium.

* * * * *

UNITED STATES PATENT AND TRADEMARK OFFICE
CERTIFICATE OF CORRECTION

| | | |
|---|---|---|
| PATENT NO. | : 7,547,523 B2 | Page 1 of 1 |
| APPLICATION NO. | : 11/620337 | |
| DATED | : June 16, 2009 | |
| INVENTOR(S) | : Jiang X. Behan et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 28 days.

Signed and Sealed this
Eighth Day of March, 2011

David J. Kappos
*Director of the United States Patent and Trademark Office*